(12) United States Patent
Jones et al.

(10) Patent No.: US 6,833,003 B2
(45) Date of Patent: Dec. 21, 2004

(54) EXPANDABLE STENT AND DELIVERY SYSTEM

(75) Inventors: Donald K. Jones, Lauderhill, FL (US); Vladimir Mitelberg, Aventura, FL (US)

(73) Assignee: Cordis Neurovascular, Miami Lakes, FL (US)

( * ) Notice: Subject to any disclaimer, the term of this patent is extended or adjusted under 35 U.S.C. 154(b) by 64 days.

(21) Appl. No.: 10/365,288

(22) Filed: Feb. 12, 2003

(65) Prior Publication Data

US 2004/0158307 A1 Aug. 12, 2004

Related U.S. Application Data (60) Provisional application No. 60/390,998, filed on Jun. 24, 2002.

(51) Int. Cl.[7] .................................................. A61F 2/06
(52) U.S. Cl. ..................................... 623/1.11; 623/1.15
(58) Field of Search .............................. 673/1.11, 1.15, 673/1.23; 606/108, 194

(56) References Cited

U.S. PATENT DOCUMENTS

| | | | |
|---|---|---|---|
| 4,768,507 A | | 9/1988 | Fischell et al. |
| 5,147,370 A | * | 9/1992 | McNamara et al. ....... 623/1.11 |
| 5,288,711 A | | 2/1994 | Mitchell et al. |
| 5,516,781 A | | 5/1996 | Morris et al. |
| 5,563,146 A | | 10/1996 | Morris et al. |
| 5,646,160 A | | 7/1997 | Morris et al. |
| 5,741,327 A | | 4/1998 | Frantzen |
| 5,935,135 A | * | 8/1999 | Bramfitt et al. ............ 623/1.11 |
| 6,126,684 A | | 10/2000 | Govin et al. |
| 6,126,685 A | | 10/2000 | Lenker et al. |
| 6,214,036 B1 | | 4/2001 | Letendre et al. |
| 6,267,783 B1 | * | 7/2001 | Letendre et al. ........... 623/1.13 |
| 6,302,893 B1 | | 10/2001 | Limon et al. |
| 6,361,558 B1 | | 3/2002 | Hieshima et al. |
| 6,395,017 B1 | | 5/2002 | Dwyer et al. |
| 6,582,460 B1 | * | 6/2003 | Cryer ........................ 623/1.11 |
| 6,702,844 B1 | * | 3/2004 | Lazarus ..................... 623/1.14 |
| 2001/0049547 A1 | * | 12/2001 | Moore ........................ 623/1.11 |
| 2002/0055767 A1 | | 5/2002 | Forde et al. |

FOREIGN PATENT DOCUMENTS

| | | |
|---|---|---|
| EP | 1 036 550 A2 | 9/2000 |
| EP | 1 157 673 A2 | 11/2001 |
| WO | WO 02/067782 A2 | 9/2002 |

OTHER PUBLICATIONS

European Search Report dated Oct. 8, 2003, for European Patent Application No. 03253777.1.

* cited by examiner

Primary Examiner—Bruce Snow
(74) Attorney, Agent, or Firm—Henry W. Collins

(57) ABSTRACT

An expandable stent and delivery system is provided for enhancing luminal dilation of a blood vessel. The delivery system includes proximal, intermediate and distal cylindrical members disposed on and spaced apart along an elongated core member such that first and second gaps are formed. The expandable stent includes proximal and distal anchor members which align with the gaps. The expandable stent is mounted on the intermediate cylindrical member, and the anchor members are disposed within the gaps thereby locking the stent onto the core member.

16 Claims, 10 Drawing Sheets

EXPANDABLE STENT AND DELIVERY SYSTEM

This patent application claims the benefit of provisional patent application Ser. No. 60/390,998 filed on Jun. 24, 2002.

BACKGROUND OF THE INVENTION

1. Field of the Invention

This invention relates to intravascular expandable devices and delivery systems for implantation within a vessel of the body, and more particularly to an expandable stent and delivery system which may be used in the treatment of blood vessel disorders. More specifically, the expandable stent and delivery system may be used in the treatment of blood vessel blockage and aneurysms which occur in the brain.

2. Description of the Prior Art

On a worldwide basis, nearly one million balloon angioplasties were performed in 1997 to treat vascular disease, including blood vessels clogged or narrowed by a lesion or stenosis. The objective of this procedure is to increase the inner diameter or cross-sectional area of the vessel passage, or lumen, through which blood flows.

In an effort to prevent restenosis without requiring surgery, short flexible cylinders or scaffolds, made of metal or polymers, are often placed into a vessel to maintain or improve blood flow. Referred to as stents, various types of these devices are widely used for reinforcing diseased blood vessels, for opening occluded blood vessels, and for defining an internal lumen to relieve pressure in an aneurysm. Stents allow blood to flow through the vessels at an improved rate while providing the desired lumen opening or structural integrity lost by the damaged vessels. Some stents are expanded to their proper size by inflating a balloon catheter, referred to as "balloon expandable" stents, while others are designed to elastically resist compression in a "self-expanding" manner.

Balloon expandable stents and self-expanding stents are generally delivered in a cylindrical form, compressed to a smaller diameter and are placed within a vessel using a catheter-based delivery system. When positioned at a desired site within a vessel, these devices are expanded by a balloon, or allowed to "self-expand," to the desired diameter.

U.S. Pat. No. 4,768,507 entitled, "Intravascular Stent and Percutaneous Insertion Catheter System for the Dilation of an Arterial Stenosis and the Prevention of Arterial Restenosis" discloses a system used for placing a coil spring stent into a vessel for the purposes of enhancing luminal dilation, preventing arterial restenosis and preventing vessel blockage resulting from intimal dissection following balloon and other methods of angioplasty. The coil spring stent is placed into spiral grooves on an insertion catheter. A back groove of the insertion catheter contains the most proximal coil of the coil spring stent which is prevented from springing radially outward by a flange. The coil spring stent is deployed when an outer cylinder is moved proximally allowing the stent to expand.

Also, U.S. Pat. No. 6,126,684 entitled, "Apparatus and Methods for Placement and Repositioning of Intraluminal Prostheses" discloses a delivery catheter for a radially compressible tubular prosthesis including an elongated shaft slideably received within an elongated sheath. The prosthesis is carried over the distal end of the shaft where it is contained in a radially compressed configuration by the sheath. Penetrating stay members on the exterior of the shaft engage the proximal section of the prosthesis allowing the prosthesis to be recaptured prior to full release of the prosthesis.

Another stent and delivery system is disclosed in U.S. Pat. No. 6,214,036 entitled, "Stent Which is Easily Recaptured and Repositioned Within the Body." This patent discloses a self-expanding stent which may be used in the treatment of aortic aneurysms. This device includes longitudinal legs having a flange which attaches to a delivery apparatus. The stent may be easily recaptured after placement and repositioned to a new position within the vessel. This patent, assigned to a related company, is subsequently referred to and the disclosure therein is incorporated and made a part of the subject patent application.

U.S. Pat. No. 6,361,558 entitled, "Stent Aneurysm Treatment System and Method" and assigned to the same assignee as the present application discloses other stent devices. This patent discloses vasculature stents of various configurations which may be used as aneurysm covers for occluding, or partially occluding, aneurysms located at various positions along the blood vessels.

SUMMARY OF THE INVENTION

In accordance with one aspect of the present invention, there is provided an expandable stent and delivery system. The delivery system includes an elongated core member having a proximal cylindrical member disposed about the core member. An intermediate cylindrical member is disposed about the core member generally positioned distally from the proximal cylindrical member and spaced apart from the proximal cylindrical member to form a first gap. A distal cylindrical member is disposed about the core member generally positioned distally from the intermediate cylindrical member and spaced apart from the intermediate cylindrical member to form a second gap.

The expandable stent includes at least one proximal leg which extends proximally from the proximal end of the stent. The stent also includes at least one distal leg which extends distally from the distal end of the stent. The stent further includes at least one anchor member attached to the proximal leg and at least one anchor member attached to the distal leg. The anchor members have a longitudinal length less than the longitudinal length of the first and second gaps and are inwardly projected in a direction toward the longitudinal axis of the stent. The stent is mounted on the intermediate cylindrical member and positioned such that the anchor members interlock within the gaps.

The delivery system further includes a deployment catheter disposed about the core member such that the deployment catheter constrains the expandable stent about the intermediate cylindrical member causing the anchor members to be maintained in the gaps and thereby causing the stent to be interlocked onto the core member.

In accordance with another aspect of the present invention, there is provided an expandable stent and delivery system. The delivery system includes an elongated core member with a proximal cylindrical member disposed about the core member. A distal cylindrical member is disposed about the core member generally positioned distally from the proximal cylindrical member and spaced apart from the proximal cylindrical member to form a gap. The expandable stent includes an anchor member attached to the stent. The anchor member has a longitudinal length less than or approximately equal to the longitudinal length of the gap and is inwardly projected in a direction toward the longitudinal axis of the stent. The stent is mounted on at least one cylindrical member and positioned such that the anchor member interlocks within the gap.

The delivery system further includes a deployment catheter disposed about the core member such that the deployment catheter constrains the expandable stent about at least one cylindrical member causing the anchor member to be maintained in the gap and thereby causing the stent to be interlocked onto the core member.

In accordance with a further aspect of the present invention, there is provided an expandable stent and delivery system. The delivery system includes an elongated core member with a plurality of cylindrical members disposed about the core member and spaced apart to form a plurality of gaps. The expandable stent includes a plurality of anchor members attached to the stent. The anchor members have a longitudinal length less than the longitudinal length of the gaps and are inwardly projected in a direction toward the longitudinal axis of the stent. The stent is mounted on at least one cylindrical member and positioned such that the anchor members interlock within the gaps.

The delivery system further includes a deployment catheter disposed about the core member such that the deployment catheter constrains the expandable stent about at least one cylindrical member causing the anchor members to be maintained in the gaps and thereby causing the stent to be interlocked onto the core member.

In accordance with a further aspect of the present invention, the elongated core member is tapered such that the proximal section of the core member has a diameter which allows the core member to be pushed through a blood vessel and the distal section of the core member has a diameter less than the diameter of the proximal section of the core member.

In accordance with still another aspect of the present invention, the expandable stent includes two proximal legs extending proximally from the proximal end of the stent and two distal legs extending distally from the distal end of the stent. Two anchor members are attached to the proximal legs, and two anchor members are attached to the distal legs. The anchor members have longitudinal lengths less than the longitudinal lengths of the gaps and are inwardly projected in a direction toward the longitudinal axis of the stent.

In accordance with another aspect of the present invention, the proximal, intermediate, and distal cylindrical members take the form of flexible coils.

In accordance with a further aspect of the present invention, a method is provided for deploying an expandable stent within a blood vessel to enhance luminal dilation of the blood vessel or to treat an aneurysm. The method includes the step of providing an expandable stent and delivery system. The expandable stent is mounted on at least one cylindrical member along a core member of the delivery system. The stent has at least one anchor member which is interlocked within at least one gap along the core member. The gaps are formed by spaces between a plurality of cylindrical members disposed on the core member. The delivery system includes a deployment catheter disposed about the stent which maintains the stent in a constrained configuration.

The method further includes the step of inserting the expandable stent and delivery system into a blood vessel and positioning the expandable stent adjacent to a blockage area or aneurysm within the vessel. The method also includes moving the deployment catheter proximally allowing the stent to begin expanding within the vessel, then again moving the deployment catheter proximally allowing the stent to fully deploy causing the vessel to increase in luminal dilation or causing the stent to cover the aneurysm. Finally, the method includes removing the delivery system from the blood vessel.

In accordance with still another aspect of the present invention, a method is provided for resheathing an expandable stent onto a delivery system within a blood vessel. The method includes the step of providing an expandable stent and delivery system. The expandable stent is mounted on at least one cylindrical member along a core member of the delivery system. The stent has at least one anchor member interlocked within at least one gap along the core member. The gap is formed by spaces between a plurality of cylindrical members disposed on the core member. The delivery system includes a deployment catheter disposed about the stent which maintains the stent in a constrained configuration. The method further includes inserting the expandable stent and delivery system into the vessel. The method also includes moving the deployment catheter proximally allowing the stent to begin expanding within the vessel. In addition, the method includes moving the deployment catheter distally which forces the stent back onto the cylindrical member of the delivery system. Finally, the method includes removing the stent and delivery system from the blood vessel or repositioning the stent and delivery system within the blood vessel.

These and other aspects of the present invention and the advantages thereof will be more clearly understood from the foregoing description in drawings of a preferred embodiment of the present invention.

DESCRIPTION OF THE PREFERRED EMBODIMENT

Figure 1:
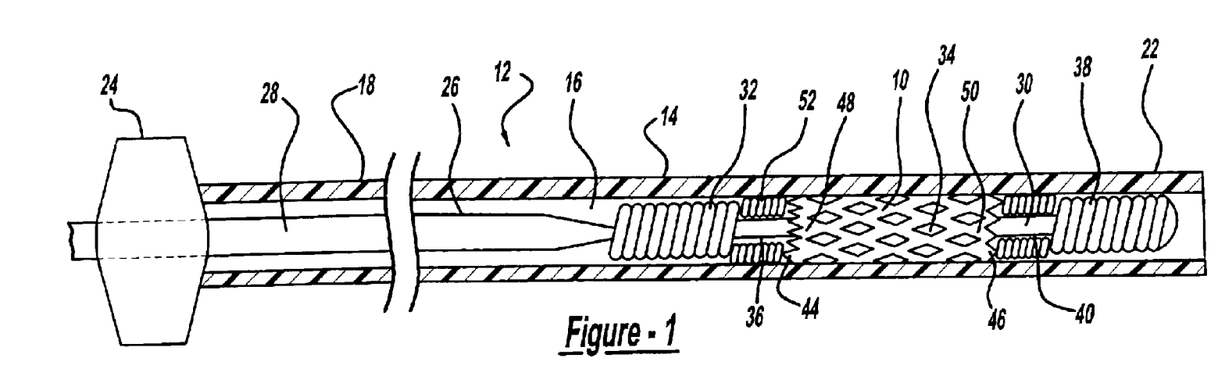
FIG. 1 is an enlarged partial sectional view of an expandable stent and delivery system in accordance with the present invention.

FIG. 1 illustrates an expandable stent 10 and delivery system 12. The delivery system 12 includes a deployment catheter 14 which is an elongated tube with a lumen 16. The lumen 16 of the deployment catheter 14 has a diameter in the range of 0.010 inches to 0.25 inches with a preferred diameter of approximately 0.021 inches. Preferably, the proximal section 18 of the deployment catheter 14 is formed of a nylon material having a durometer in a range of about 60D to 75D. The proximal section 18 is sufficiently flexible to traverse a blood vessel, but is sufficiently rigid so that it can be pushed distally through a blood vessel. The distal section 22 of the deployment catheter 14 is preferably formed of a pellethane material having a durometer of between 25D and 55D with a durometer of 40D being the preferred durometer.

The delivery system 12 includes a winged hub 24 coupled to the proximal section 18 of the deployment catheter 14. The winged hub 24 may be made from plastic and aids in the insertion of the deployment catheter 14 into a blood vessel. The delivery system 12 also includes an elongated core member 26 which is a wire preferably made of Nitinol but may also be made from other metal alloys or a polymer material. The core member 26 is slideably disposed within the lumen 16 of the deployment catheter 14. The core member 26 may have a long taper or may have multiple tapers to give the proximal section 28 of the core member 26 a greater diameter than the distal section 30 of the core member 26. Preferably, the diameter of the proximal section 28 of the core member 26 is approximately 0.016 inches while the diameter of the distal section 30 is about 0.002 inches. The greater diameter of the proximal section 28 gives the core member 26 sufficient stiffness to be pushed through the deployment catheter 14, and the smaller diameter of the distal section 30 provides flexibility for the core member 26 to traverse narrow blood vessels.

The delivery system 12 further includes a proximal cylindrical member 32 disposed about the distal section 30 of the core member 26. Preferably, the proximal cylindrical member 32 is a helically wound flexible coil with an outside diameter of about 0.016 inches. The coil may be made of a polymer material but the preferred material is metal. An intermediate cylindrical member 34 (located within the stent and not seen in this figure) is also disposed about the core member 26 distally from the proximal cylindrical member 32 and spaced apart from the proximal cylindrical member 32. The intermediate cylindrical member 34 may be a cylindrical sleeve or a coil with an outside diameter of approximately 0.012 inches. The space between the proximal and intermediate cylindrical members 32 and 34 along the core member 26 forms a first gap 36. The length of the first gap 36 may range from 0.019 inches to 0.19 inches with a preferred length of 0.040 inches.

A distal cylindrical member 38 is also disposed about the core member 26 distally from the intermediate cylindrical member 34 and spaced apart from the intermediate cylindrical member 34. Preferably, the distal cylindrical member 38 is a helically wound flexible coil with an outside diameter of about 0.016 inches. The coil may be made of a polymer material but the preferred material is metal. The space between the intermediate and distal cylindrical members 34 and 38 along the core member 26 forms a second gap 40. The length of the second gap 40 may range from 0.019 inches to 0.19 inches with a preferred length of 0.040 inches. The distal cylindrical member 38 may also be shapeable so that the core member 26 may be used as a guidewire. For example, the distal cylindrical member 38 may be slightly angled to permit the core member 26 to navigate through the vasculature of the body.

An expandable stent 10 is mounted on the intermediate cylindrical member 34. The expandable stent 10 may take on many different patterns or configurations. Examples of such stents are disclosed in U.S. patent applications, "Intravascular Stent Device" filed Jun. 5, 2002. The disclosures in these applications are incorporated herein by reference. The expandable stent 10 is preferably laser cut from a tubular piece of Nitinol and thereafter treated so as to exhibit superelastic properties at body temperature. The expandable stent 10 may include proximal and distal legs 44 and 46 that are attached to the proximal and distal ends 48 and 50 of the stent 10 and extend along the longitudinal axis of the stent 10. The expandable stent 10 also includes anchor members 52 which are either attached to the ends 48 and 50 of the stent 10 or to the proximal and distal legs 44 and 46 of the stent 10. In addition, anchor members 52 may be positioned at other locations along the stent between ends 48 and 50. The anchor members 52 may be projections made from polymer or metallic material which extend generally parallel to the longitudinal axis the stent 10 and extend downward toward the longitudinal axis of the stent 10.

Preferably, the anchor members 52 are helically wound flexible coils and made of a radiopaque material for use during fluoroscopic visualization. As the expandable stent 10 is positioned and mounted on the intermediate cylindrical member 34, the anchor members 52 attached to the proximal end 48 or proximal legs 44 of the stent 10 align with and are disposed within the first gap 36. Similarly, the anchor members 52 attached to the distal end 50 or distal legs 46 of the stent 10 align with and are disposed within the second gap 40. In this configuration, the expandable stent 10 is locked in place and can be pushed and pulled through the deployment catheter 14 without damaging or deforming the stent 10.

It should be understood that the expandable stent 10 of the present invention may alternatively be coated with an agent, such as heparin or rapamycin, to prevent stenosis or restenosis of the vessel. Examples of such coatings are disclosed in U.S. Pat. Nos. 5,288,711; 5,516,781; 5,563,146 and 5,646,160. The disclosures in these patents are incorporated herein by reference.

Figure 2:
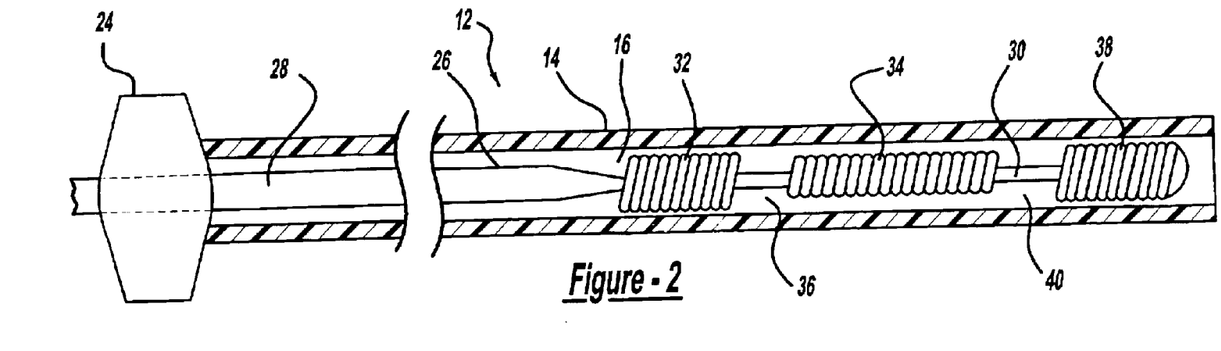
FIG. 2 is an enlarged partial sectional view of the delivery system with an intermediate cylindrical member which takes the form of a helically wound flexible coil.

FIG. 2 illustrates the delivery system 12 without the expandable stent. The delivery system 12 includes an elongated core member 26 disposed within a lumen 16 of the deployment catheter 14. Proximal, intermediate and distal cylindrical members 32, 34 and 38 are disposed about the core member 26 and spaced apart from each other such that first and second gaps 36 and 40 are formed. In the embodiment shown in this figure, the intermediate cylindrical member 34 is a helically wound flexible coil. Preferably, the flexible coil is made of a metallic material and has a length approximately equal to the length of the expandable stent 10. When the expandable stent (not shown) is mounted on the intermediate cylindrical member 34, the stent is constrained about the coil by the deployment catheter 14. In this configuration, the stent and delivery system 12 remain sufficiently flexible to traverse tortuous blood vessels.

Figure 3:
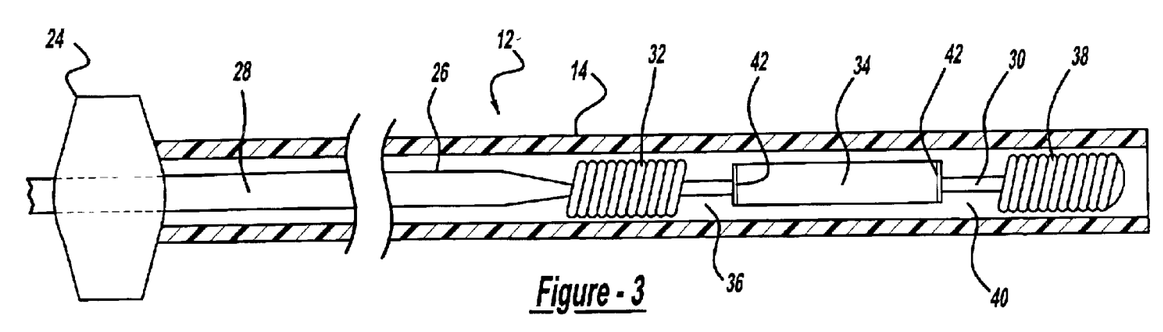
FIG. 3 is an enlarged partial sectional view of the delivery system with an intermediate cylindrical member which takes the form of a flexible cylindrical sleeve.

FIG. 3, like FIG. 2, illustrates the delivery system 12 without the expandable stent. However, in the embodiment shown in this figure, the intermediate cylindrical member 34 is a flexible cylindrical sleeve. Preferably, the cylindrical sleeve is made of a polymer material and has a smooth outer surface. The length of the cylindrical sleeve is approximately equal to the length of the expandable stent. When the expandable stent (not shown) with a drug coating is mounted on the intermediate cylindrical member 34, the stent is constrained about the cylindrical sleeve by the deployment catheter 14. In this configuration, the drug coating on the expandable stent is protected from damage caused by friction between the stent and a non-smooth intermediate cylindrical member 34 and friction between various components of the stent itself.

Reinforcing members 42 may be disposed on the ends of the proximal, intermediate and distal cylindrical members 32, 34 and 38. The reinforcing members 42 may take the form of rings or disks and may be made of a polymer or metallic material, but preferably the reinforcing members. 42 are made of the same material as the cylindrical members 32, 34 and 38. The reinforcing members 42 provide support to the ends of cylindrical members 32, 34 and 38 so that the ends resist deformation.

Figure 4:
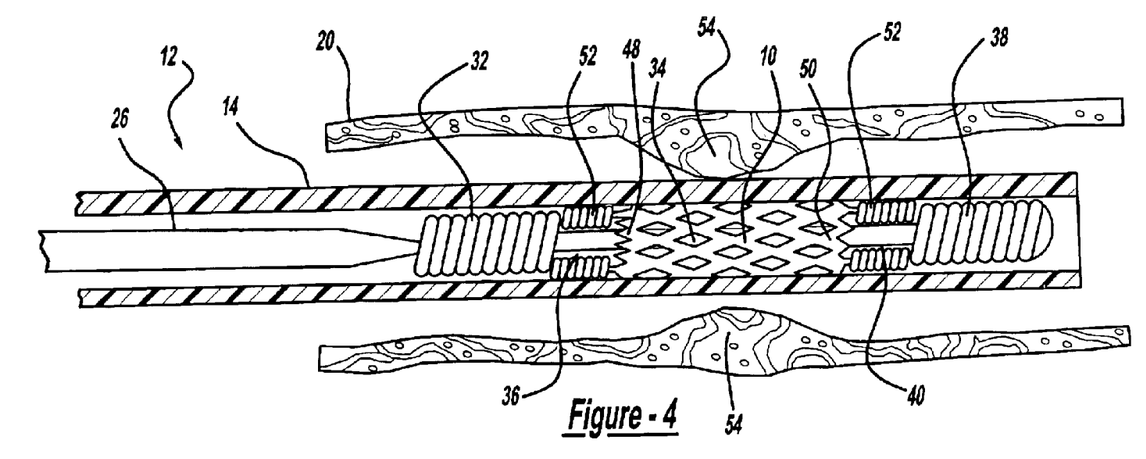
FIG. 4 is an enlarged partial sectional view of the expandable stent and delivery system disposed within a blood vessel and aligned adjacent to vessel blockage.

FIG. 4 illustrates the expandable stent 10 and delivery system 12 positioned within a blood vessel 20. The expandable stent 10 is mounted on the intermediate cylindrical member 34 (located within the stent and not seen in this figure). The anchor members 52 on the proximal end 48 of the stent 10 are disposed in the first gap 36, while the anchor members 52 on the distal end 50 of the stent 10 are disposed in the second gap 40. In this position, the stent 10 is locked into place on the core member 26. The expandable stent 10 is generally aligned with a blockage area 54 of the blood vessel 20.

Figures 5, 6:
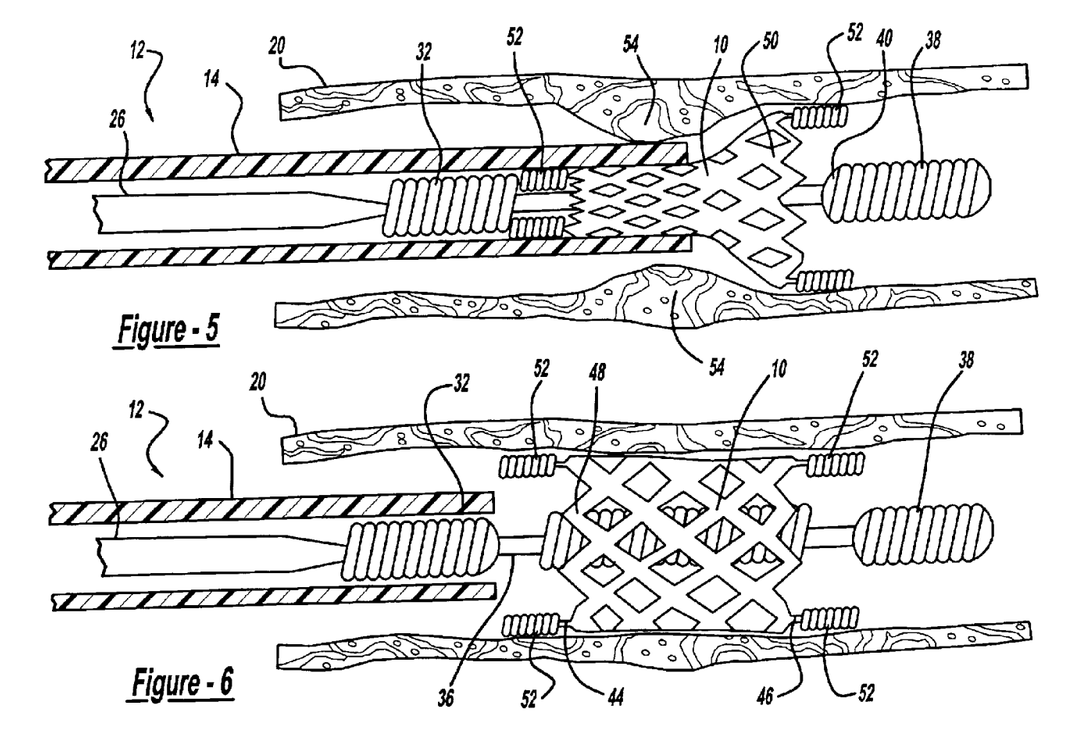
FIG. 5 is an enlarged partial sectional view of a deployment catheter moved proximally with the proximal section of the expandable stent compressed within the deployment catheter and the distal section of the expandable stent expanded within the vessel.
FIG. 6 is an enlarged sectional view of the deployment catheter moved proximally with the expandable stent expanded within the vessel.

FIG. 5 illustrates the expandable stent 10 partially deployed within the blood vessel 20. The deployment catheter 14 is moved proximally causing the anchor members 52 on the distal end 50 of the stent 10 to exit the second gap 40 thereby allowing the stent 10 to partially deploy.

FIG. 6 illustrates the expandable stent 10 fully deployed within the blood vessel 20 and the delivery system 12 still within the vessel 20. The deployment catheter 14 is moved proximally causing the anchor members 52 on the proximal end 48 of the stent 10 to exit the first gap 36 thereby allowing the stent 10 to become fully deployed.

Figure 7:
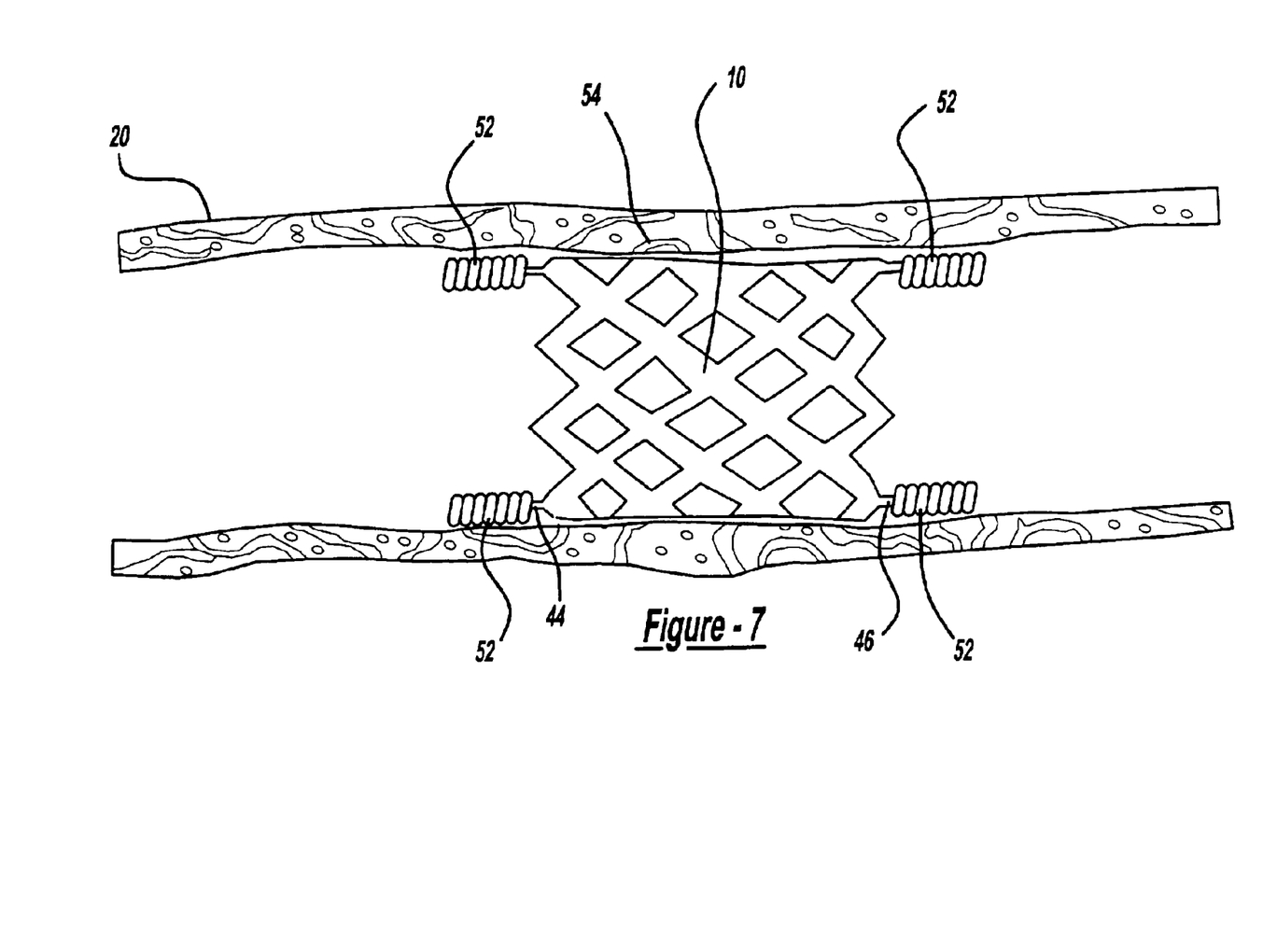
FIG. 7 is an enlarged sectional view of the stent expanded within the vessel and the delivery system removed from the vessel.

FIG. 7 illustrates the expandable stent 10 deployed within the blood vessel 20 with the delivery system 12 removed from the blood vessel 20. The expanding force of the stent 10 pushes the blockage area 54 radially outward thereby opening the blood vessel 20 for greater blood flow.

Figure 8:
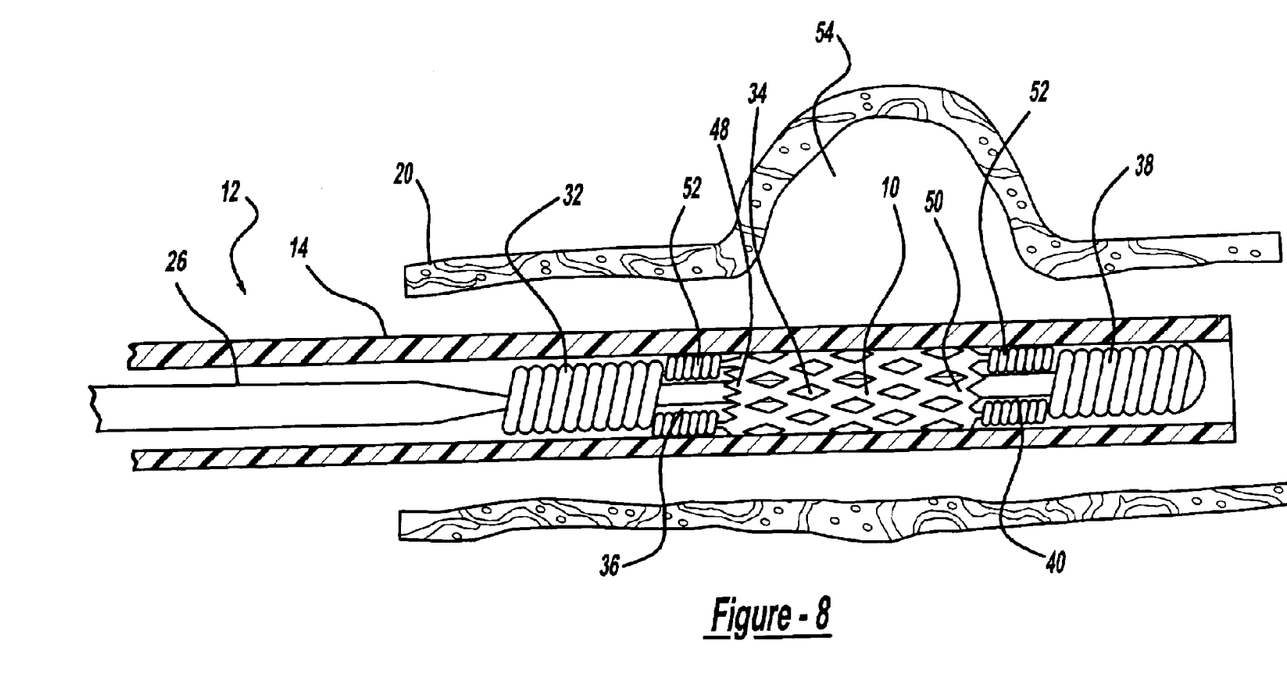
FIG. 8 is an enlarged partial sectional view of the expandable stent and delivery system disposed within a blood vessel and aligned adjacent to an aneurysm.

FIG. 8 illustrates the expandable stent 10 and delivery system 12 positioned within a blood vessel 20 and aligned with an aneurysm 56. The expandable stent 10 is mounted on the intermediate cylindrical member 34 (located within the stent and not seen in this figure). The anchor members 52 on the proximal end 48 of the stent 10 are disposed in the first gap 36, while the anchor members 52 on the distal end 50 of the stent 10 are disposed in the second gap 40. In this position, the stent 10 is locked into place on the core member 26. The expandable stent 10 is generally aligned with an aneurysm 56.

Figure 9:
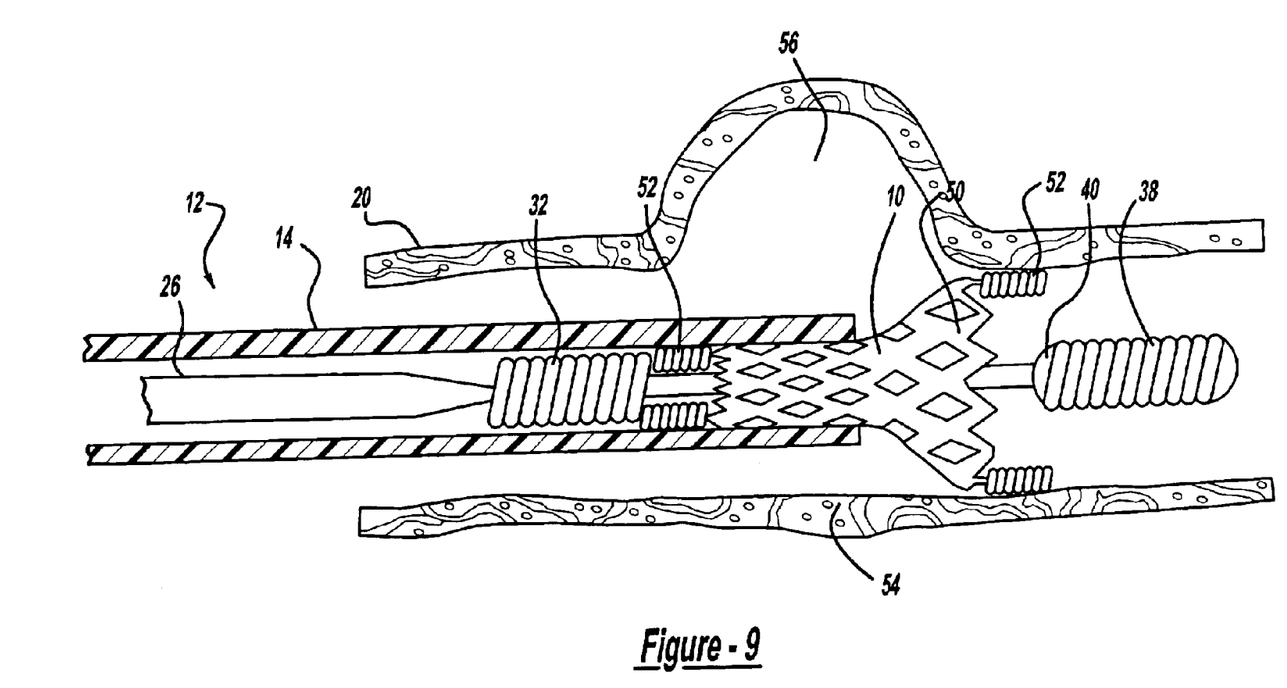
FIG. 9 is an enlarged partial sectional view of the a deployment catheter moved proximally with the proximal section of the expandable stent constrained within the deployment catheter and the distal section of the expandable stent expanded within the vessel.

FIG. 9 illustrates the expandable stent 10 partially deployed within the blood vessel 20. The deployment catheter 14 is moved proximally causing the anchor members 52 on the distal end 50 of the stent 10 to exit the second gap 40 thereby allowing the stent 10 to partially deploy and to begin covering the aneurysm 56.

Figure 10:
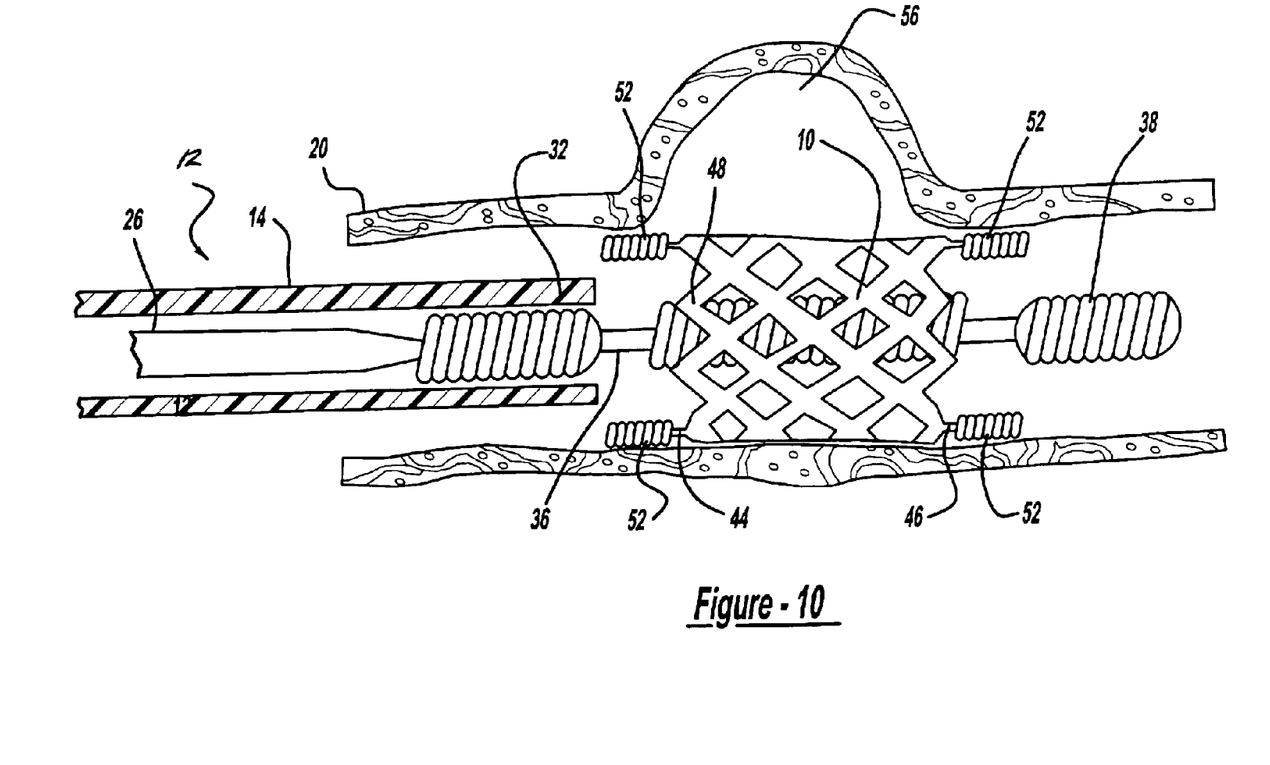
FIG. 10 is an enlarged sectional view of the deployment catheter moved proximally with the expandable stent expanded within the vessel and covering the mouth of the aneurysm.

FIG. 10 illustrates the expandable stent 10 fully deployed within the blood vessel 20 and the delivery system 12 still within the vessel 20. The deployment catheter 14 is moved proximally causing the anchor members 52 on the proximal end 48 of the stent 10 to exit the first gap 36 thereby allowing the stent 10 to become fully deployed and cover the aneurysm 56.

Figure 11:
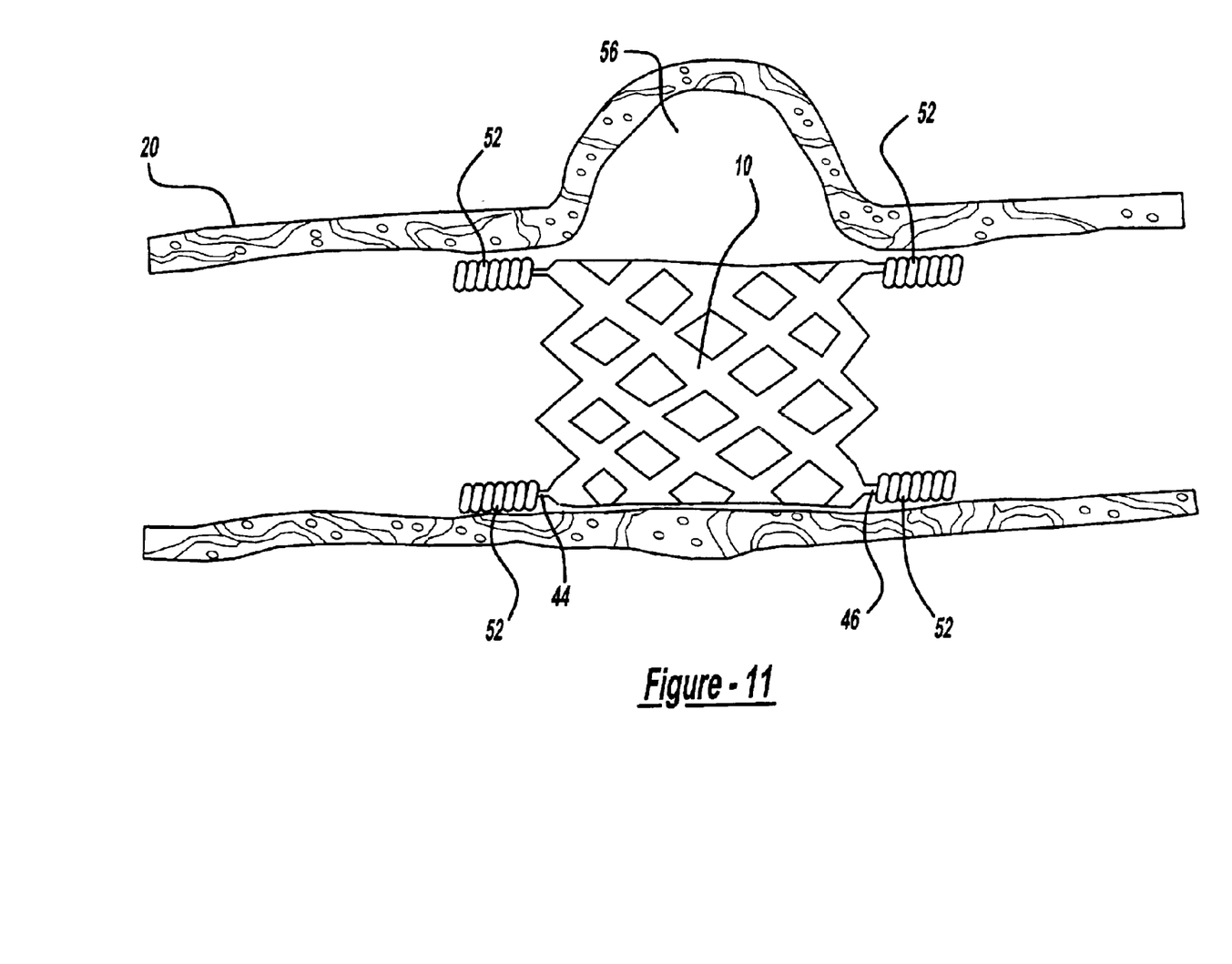
FIG. 11 is an enlarged sectional view of the stent expanded within the vessel and covering the aneurysm.

FIG. 11 illustrates the expandable stent 10 deployed within the blood vessel 20 with the delivery system 12 removed from the blood vessel 20. The expanded stent 10 covers the mouth of the aneurysm 56.

Figure 12:
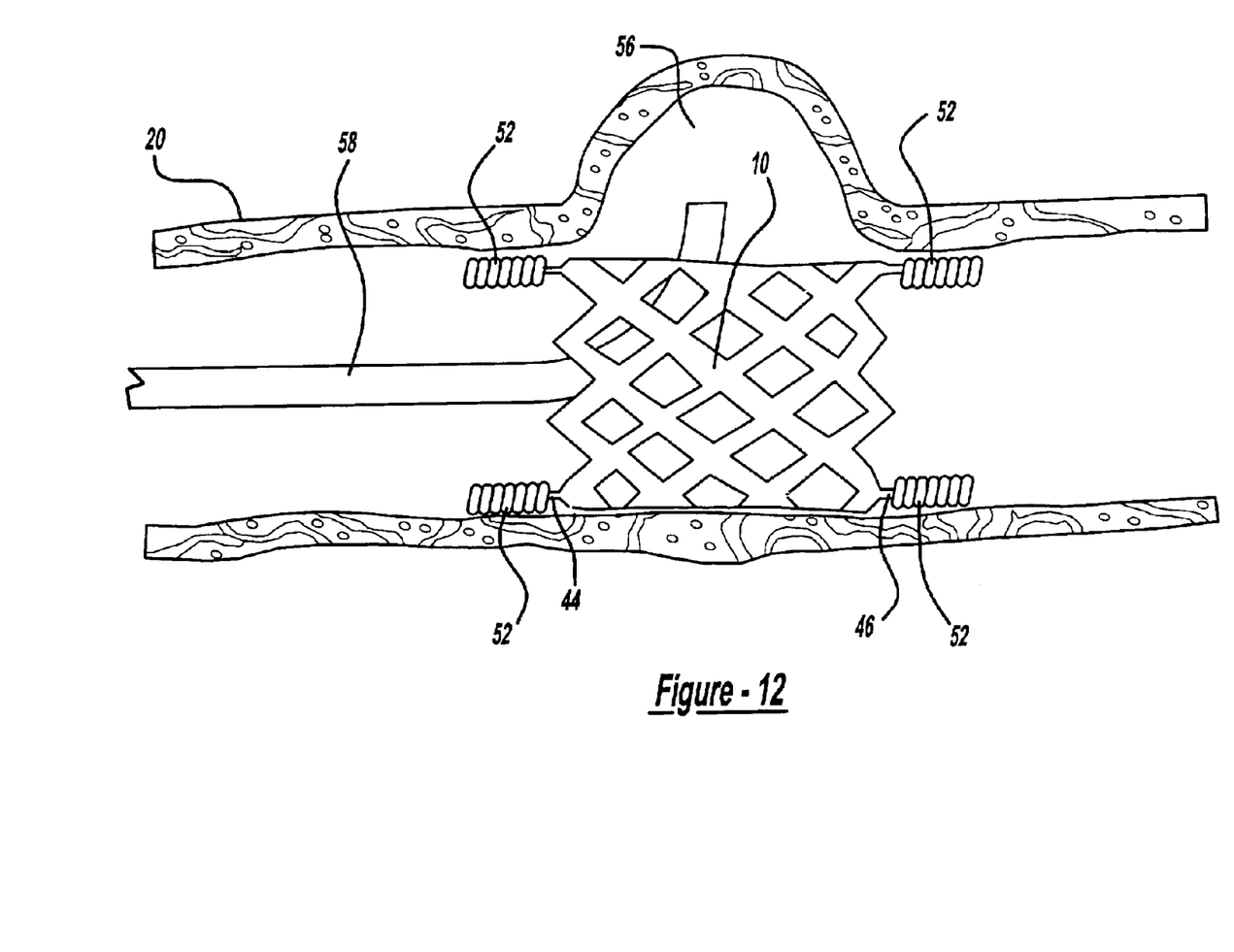
FIG. 12 is an enlarged sectional view of the stent expanded within the vessel and a microcatheter inserted through the wall of the stent and into the aneurysm; and, FIG. 13 is an enlarged sectional view of the stent expanded within the vessel and covering the aneurysm with an embolic coil deployed within the aneurysm.

FIG. 12 illustrates the expandable stent 10 deployed with the blood vessel 20 with a microcatheter 58 inserted into the blood vessel 20, through the wall of the stent 10, and into the aneurysm 56. In this position, embolic agents and medical devices may be delivered into the aneurysm 56.

Figure 13:
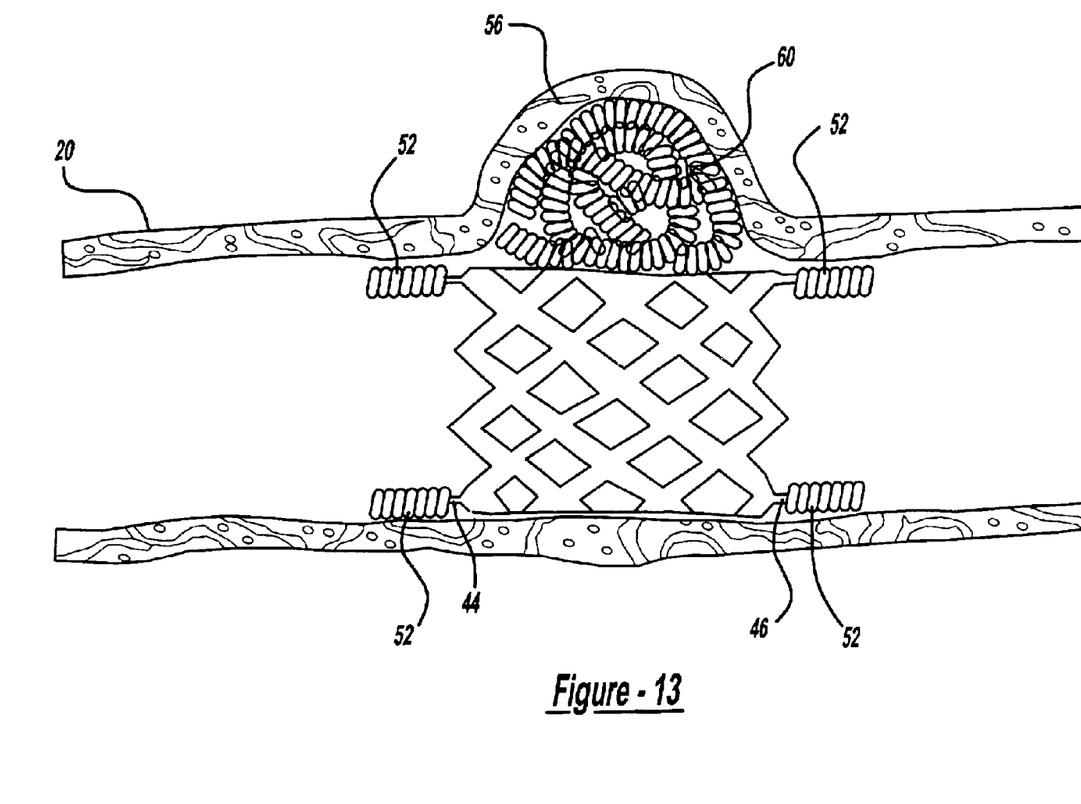

FIG. 13 illustrates the expandable stent 10 deployed with the blood vessel 20 and covering the aneurysm 56. An embolic coil 60 is deployed within the aneurysm 56 and is confined within the aneurysm 56 by the expandable stent 10.

The present invention is useful for positioning an expandable stent within a blood vessel to enhance luminal dilation of the vessel or to treat an aneurysm. To deploy the expandable stent, first the stent is mounted about the intermediate cylindrical member along the core member. The anchor members attached to the ends of the stent are aligned with the first and second gaps which are formed by the proximal, intermediate, and distal cylindrical members. The expandable stent is interlocked onto the core member while the deployment catheter is disposed about the stent holding the stent in its constrained configuration. The delivery system is then inserted into the blood vessel until the stent is aligned with the blockage area or aneurysm which is to be treated. Once positioned, the deployment catheter is moved proximally which allows the distal portion of the stent to begin expanding and permits the anchor members attached to the distal legs of the stent to become released from the second gap. During expansion, the distal portion of the stent comes in contact with the wall of the blood vessel. The deployment catheter is again moved proximally until the proximal portion of the stent expands and allows the anchor members attached to the proximal legs of the stent to become released from the first gap. The stent is now fully deployed and the delivery system may be withdrawn from the blood vessel.

The present invention is also useful in resheathing the expandable stent during the deployment process. Here, the stent is positioned on the core member as described above. Once the delivery system is positioned within the blood vessel at the blockage area or aneurysm to be treated, the deployment catheter is moved proximally to allow the distal portion of the stent to expand. If the deployment catheter is not moved proximally beyond the anchor members attached to the proximal legs of the stent, then the stent remains interlocked on the core wire. In this configuration, the stent can be resheathed and deployed at a different location within the blood vessel. To do this, the deployment catheter is moved distally forcing the stent back onto the intermediate cylindrical member and positioning the anchor members attached to the distal legs of the stent to become interlocked within the second gap. In this configuration, the expandable stent and delivery system may be withdrawn or repositioned within the blood vessel.

A novel system has been disclosed in which an expandable stent is positioned within a blood vessel. Although a preferred embodiment of the invention has been described, it is to be understood that various modifications may be made by those skilled in the art without departing from the scope of the claims which follow.

What is claimed is:

1. An expandable stent and delivery system comprising:
   an elongated core member having proximal and distal sections;
   a proximal cylindrical member disposed about the distal section of said core member;
   an intermediate cylindrical member disposed about the distal section of said core member and generally positioned on said core member distally from said proximal cylindrical member and spaced apart from said proximal cylindrical member to form a first gap having a longitudinal length;
   a distal cylindrical member disposed about the distal section of said core member and generally positioned on said core member distally from said intermediate cylindrical member and spaced apart from said intermediate cylindrical member to form a second gap having a longitudinal length;
   an expandable stent having proximal and distal ends and a longitudinal axis, said stent including at least one proximal leg taking the form of an elongated projection and extending proximally from the proximal end of said stent, said stent also including at least one distal leg taking the form of an elongated projection extending distally from the distal end of said stent, said stent further including at least one anchor member attached to said proximal leg and taking the form of an extension having a longitudinal length less than the longitudinal length of said first gap and inwardly projected in a direction toward the longitudinal axis of said stent, said stent also including at least one anchor member attached to said distal leg and taking the form of an extension having a longitudinal length less than the longitudinal length of said second gap and inwardly projected in a direction toward the longitudinal axis of said stent, said stent mounted on said intermediate cylindrical member and positioned such that said anchor members interlock within said gaps; and,
   a deployment catheter having a lumen extending therethrough and disposed about said core member such that said deployment catheter constrains said expandable stent about said intermediate cylindrical member causing said anchor members to be maintained in said gaps and thereby causing said stent to be interlocked onto said core member.

2. An expandable stent and delivery system as defined in claim 1, wherein said intermediate cylindrical member takes the form of a flexible coil having proximal and distal ends.

3. An expandable stent and delivery system as defined in claim 1, wherein said elongated core member is tapered such that the proximal section of said core member has a diameter which allows said core member to be pushed through a blood vessel and the distal section of said core member has a diameter less than the diameter of the proximal section of said core member.

4. An expandable stent and delivery system as defined in claim 1, wherein said expandable stent includes two proximal legs taking the form of elongated projections and extending proximally from the proximal end of said stent.

5. An expandable stent and delivery system as defined in claim 4, wherein said expandable stent includes two anchor members attached to said proximal legs and taking the form of extensions having longitudinal lengths less than the longitudinal length of said first gap and inwardly projected in a direction toward the longitudinal axis of said stent.

6. An expandable stent and delivery system as defined in claim 1, wherein said expandable stent includes two distal legs taking the form of elongated projections and extending distally from the distal end of said stent.

7. An expandable stent and delivery system as defined in claim 6, wherein said expandable stent includes two anchor members attached to said distal legs and taking the form of extensions having longitudinal lengths less than the longitudinal length of said second gap and inwardly projected in a direction toward the longitudinal axis of said stent.

8. An expandable stent and delivery system as defined in claim 1, wherein said proximal cylindrical member takes the form of a flexible coil.

9. An expandable stent and delivery system as defined in claim 1, wherein said distal cylindrical member takes the form of a flexible coil.

10. An expandable stent and delivery system comprising:
    an elongated core member having proximal and distal sections;
    a proximal cylindrical member disposed about the distal section of said core member;
    an intermediate cylindrical member disposed about the distal section of said core member and generally positioned on said core member distally from said proximal cylindrical member and spaced apart from said proximal cylindrical member to form a first gap having a longitudinal length;
    a distal cylindrical member disposed about the distal section of said core member and generally positioned on said core member distally from said proximal cylindrical member and spaced apart from said proximal cylindrical member to form a second gap having a longitudinal length;
    an expandable stent having a longitudinal axis, said stent including an anchor member attached to said stent and taking the form of an extension having a longitudinal length less than the longitudinal length of said first gap and inwardly projected in a direction toward the longitudinal axis of said stent, said stent mounted on said intermediate cylindrical member and positioned such that said anchor member interlocks within said first gap; and,
    a deployment catheter having a lumen extending therethrough and disposed about said core member such that said deployment catheter constrains said expandable stent about at least one cylindrical member causing said anchor member to be maintained in said first gap and thereby causing said stent to be interlocked onto said core member.

11. An expandable stent and delivery system as defined in claim 10, wherein at least one cylindrical member takes the form of a flexible coil having proximal and distal ends.

12. An expandable stent and delivery system as defined in claim 10, wherein said elongated core member is tapered such that the proximal section of said core member has a diameter which allows said core member to be pushed through a blood vessel and the distal section of said core member has a diameter less than the diameter of the proximal section of said core member.

13. An expandable stent and delivery system comprising:
    an elongated core member having proximal and distal sections;

a proximal cylindrical member disposed about the distal section of said core member;

an intermediate cylindrical member disposed about the distal section of said core member and generally positioned on said core member distally from said proximal cylindrical member and spaced apart from said proximal cylindrical member to form a first gap having a longitudinal length;

a distal cylindrical member disposed about the distal section of said core member and generally positioned on said core member distally from said proximal cylindrical member and spaced apart from said proximal cylindrical member to form a second gap having a longitudinal length;

an expandable stent having a longitudinal axis, said stent including an anchor member attached to said stent and taking the form of an extension having a longitudinal length approximately equal to the longitudinal length of said second gap and inwardly projected in a direction toward the longitudinal axis of said stent, said stent mounted on said intermediate cylindrical member and positioned such that said anchor member interlocks within said second gap; and, a deployment catheter having a lumen extending therethrough and disposed about said core member such that said deployment catheter constrains said expandable stent about at least one cylindrical member causing said anchor member to be maintained in said second gap and thereby causing said stent to be interlocked onto said core member.

14. An expandable stent and delivery system as defined in claim 13, wherein at least one cylindrical member takes the form of a flexible coil having proximal and distal ends.

15. An expandable stent and delivery system as defined in claim 13, wherein said elongated core member is tapered such that the proximal section of said core member has a diameter which allows said core member to be pushed through a blood vessel and the distal section of said core member has a diameter less than the diameter of the proximal section of said core member.

16. An expandable stent and delivery system comprising:

an elongated core member having proximal and distal sections;

a plurality of cylindrical members disposed about the distal section of said core member and spaced apart to form a plurality of gaps each having a longitudinal length;

an expandable stent having a longitudinal axis, said stent including a plurality of anchor members attached to said stent and taking the form of extensions having a longitudinal length less than the longitudinal length of said gaps and inwardly projected in a direction toward the longitudinal axis of said stent, said stent mounted on at least one cylindrical member and positioned such that said anchor members interlock within said gaps; and, a deployment catheter having a lumen extending therethrough and disposed about said core member such that said deployment catheter constrains said expandable stent about at least one cylindrical member causing said anchor members to be maintained in said gaps and thereby causing said stent to be interlocked onto said core member.

* * * * *